United States Patent
Nicholas et al.

(10) Patent No.: US 11,639,322 B2
(45) Date of Patent: May 2, 2023

(54) SULFURIC ACID CATALYZED ALKYLATION PROCESS

(71) Applicant: UOP LLC, Des Plaines, IL (US)

(72) Inventors: Christopher P. Nicholas, Evanston, IL (US); Susie C. Martins, Carol Stream, IL (US); David E. Mackowiak, Mount Prospect, IL (US); Hayim Abrevaya, Kenilworth, IL (US); Joel T. Walenga, Lake Zurich, IL (US)

(73) Assignee: UOP LLC, Des Plaines, IL (US)

( * ) Notice: Subject to any disclaimer, the term of this patent is extended or adjusted under 35 U.S.C. 154(b) by 27 days.

(21) Appl. No.: 17/470,034

(22) Filed: Sep. 9, 2021

(65) Prior Publication Data
US 2023/0080919 A1  Mar. 16, 2023

(51) Int. Cl.
*C07C 2/62* (2006.01)

(52) U.S. Cl.
CPC .......... *C07C 2/62* (2013.01); *C07C 2527/054* (2013.01)

(58) Field of Classification Search
CPC .............................. C07C 2/62; C07C 2527/054
See application file for complete search history.

(56) References Cited

U.S. PATENT DOCUMENTS

| | | | | |
|---|---|---|---|---|
| 3,689,590 A * | 9/1972 | Rakow | ...................... | C07C 2/62 585/731 |
| 4,041,102 A * | 8/1977 | Wronka | ................. | C07C 7/1485 585/854 |
| 4,357,482 A * | 11/1982 | Kramer | ...................... | C07C 2/62 585/731 |
| 4,426,545 A * | 1/1984 | Kramer | ...................... | C07C 2/62 585/731 |
| 4,467,132 A * | 8/1984 | Go | ............................. | C07C 2/62 585/458 |
| 4,544,794 A * | 10/1985 | Miller | ....................... | C07C 2/62 585/458 |
| 4,544,795 A * | 10/1985 | Miller | ....................... | C07C 2/62 585/458 |
| 4,560,825 A * | 12/1985 | Kramer | ................ | B01J 31/0225 585/731 |
| 4,595,512 A * | 6/1986 | Tellier | .................... | C09K 8/601 516/26 |

(Continued)

OTHER PUBLICATIONS

Hejazifar et al. (J. Org. Chem. 2016, 81, 12332-12339) (Year: 2016).*

(Continued)

*Primary Examiner* — Ali Z Fadhel

(57) ABSTRACT

A process for sulfuric acid catalyzed alkylation involving the use of surfactants which form bi-continuous micro-emulsions with the sulfuric acid and the hydrocarbon is described. The bi-continuous phase facilitates and improves the sulfuric acid catalyzed alkylation reactions. The concentration of the surfactant is selected based on the type of olefin feed. Easy to alkylate feeds, such as 2-butene, use lower concentrations of surfactant, while feeds which are harder to alkylate, such as propene or isobutene, use higher concentrations of the surfactant. In addition, increasing the concentration of sulfuric acid when a surfactant is included resulted in higher calculated RON. The use of a surfactant and a high concentration of sulfuric acid can provide a calculated RON over 100 and close to theoretical yields.

20 Claims, 5 Drawing Sheets

(56) References Cited

U.S. PATENT DOCUMENTS

| | | | | |
|---|---|---|---|---|
| 4,650,918 | A * | 3/1987 | Miller | C07C 2/62 585/458 |
| 4,675,305 | A * | 6/1987 | Miller | C07C 2/54 502/168 |
| 4,795,728 | A * | 1/1989 | Kocal | B01J 31/0271 585/724 |
| 4,835,333 | A * | 5/1989 | Kocal | B01J 31/40 585/724 |
| 4,885,425 | A * | 12/1989 | Young | C23F 11/04 585/458 |
| 4,891,466 | A * | 1/1990 | Kocal | C07C 2/62 585/723 |
| 5,094,295 | A * | 3/1992 | Morrow | C08H 6/00 166/275 |
| 5,120,895 | A * | 6/1992 | Child | B01J 10/002 585/731 |
| 6,194,625 | B1 | 2/2001 | Graves et al. | |
| 2009/0163758 | A1 | 6/2009 | Bakshi | |
| 2019/0001314 | A1 | 1/2019 | Buchbinder et al. | |
| 2020/0231520 | A1 | 7/2020 | Rana et al. | |
| 2020/0239382 | A1 * | 7/2020 | Bhattacharyya | C07C 2/70 |

OTHER PUBLICATIONS

Minnick, David L. et al., Understanding Sulfur Content in Alkylate from Sulfuric Acid-Catalyzed C3/C4 Alkylations, Energy Fuels 2019, 33, 4659-4670.

Pizzino, Aldo et al., Relationship between Phase Behavior and Emulsion Inversion for a Well-Defined Surfactant (C10E4)/-Octane/Water Ternary System at Different Temperatures and Water/Oil Ratios, Ind. Eng. Chem. Res. 2013, 52, 4527-4538.

Zhao, Yu et al., Improvement of product distribution though enhanced mass transfer in isobutane/butene alkylation, Chemical Engineering Research and Design 143 (2019) 190-200.

Zheng, Weizhong et al., H2SO4-catalyzed isobutane alkylation under low temperatures promoted by long-alkyl-chain surfactant additives, Reaction Engineering, Kinetics and Catalysis, AlChE, J., 2021, e17349, https://doi.org/10.1002/ aic. 17349.

Albright, Lyle F. et al., Formation and Separation of Sulfuric Acid/n-Heptane Dispersions: Applications to Alkylation, Ind Eng Chem Res 2001, 40, 4032-4039.

Salager, Jean-Louis et al., Current Phenomenological Know-How and Modeling of Emulsion Invesion, Ind. Eng. Chem. Res. 2000, 39, 2665-2676.

Kranz, Ken. E. et al., Alkylation of Isobutane with Light Olefins: Yields of Alkylates for Different Olefins, Ind. Eng. Chem. Res. 1993, 32, 2991-2996.

Albright, Lyle F. et al., Alkylation of Isobutane with C4 Olefins. 3. Two-Step Process Using Sulfuric Acid as Catalyst, Ind Eng Chem Res. 1988, 27, 391-397.

International Search Report from corresponding PCT application No. PCT/US2022/075895, dated Dec. 21, 2022.

Written Opinion from corresponding PCT application No. PCT/US2022/075895, dated Dec. 19, 2022.

* cited by examiner

SULFURIC ACID CATALYZED ALKYLATION PROCESS

BACKGROUND

Alkylation is typically used to combine light olefins, for example mixtures of alkenes such as propylene and butylene, with isobutane to produce a relatively high-octane branched-chain paraffinic hydrocarbon fuel, including isoheptane and isooctane. Similarly, an alkylation reaction can be performed using an aromatic compound such as benzene in place of the isobutane. When using benzene, the product resulting from the alkylation reaction is an alkylbenzene (e.g. ethylbenzene, cumene, dodecylbenzene, etc.).

The alkylation of paraffins with olefins for the production of alkylate for gasoline can use a variety of catalysts. The choice of catalyst depends on the end product a producer desires. Typical alkylation catalysts used since the 1940s include concentrated sulfuric acid or hydrofluoric acid.

Solid catalysts are also used for alkylation. However, solid catalysts are generally rapidly deactivated by the presence of water, which may be present in the feed.

Acidic ionic liquids can be used as an alternative to the commonly used strong acid catalysts in alkylation processes. Ionic liquids are salts comprised of cations and anions which typically melt below about 100° C. Ionic liquids are essentially salts in a liquid state, and are described in U.S. Pat. Nos. 4,764,440, 5,104,840, and 5,824,832. The properties vary extensively for different ionic liquids, and the use of ionic liquids depends on the properties of a given ionic liquid. Depending on the organic cation of the ionic liquid and the anion, the ionic liquid can have very different properties.

In the case where sulfuric acid is the alkylation catalyst, the alkylation reaction rate is limited by the low solubility of isoalkanes in sulfuric acid, and rigorous agitation is required to create a large interfacial area to allow for sufficient mass transfer. It is known that certain compounds, herein referred to as surfactants, may be employed in admixture with the acid catalyst in an alkylation process to improve the production of alkylate at the expense of olefin polymers and the resulting light and heavy compounds. Also, the use of such alkylation aids decreases the consumption of catalyst in an alkylation process. For example, a variety of surfactant compounds which may be used in alkylation processes are described in U.S. Pat. Nos. 2,880,255; 3,661,514; 2,981,772; 3,231,633; 3,364,280; 3,324,196; and 3,926,839.

Surfactants are well known to aid mass transfer between the phases by the creation of micelles and are the subject of numerous patents and academic studies over the past 70 years (Chen, W.-S. Solubility measurements of isobutane/alkenes in sulfuric acid: applications to alkylation Appl. Catal. A 2003, 255, 231-237). Surfactants may also serve to increase solubility of reactant hydrocarbons within the liquid catalyst phase. As a consequence, such surfactants must be used with care since relatively small quantities tend to create stable emulsions of reactant hydrocarbon and acid catalyst under the conditions of agitation and mixing commonly employed in commercial alkylation reactions. Such hydrocarbon acid emulsions may be difficult to break, thus complicating separation of the acid catalyst from the hydrocarbon effluent of an alkylation process.

Surfactant carry-over can cause problems in other sections of the alkylation complex. As a consequence, surfactants do not appear to be used commercially.

Therefore, there is a need for an improved alkylation process.

DESCRIPTION OF THE INVENTION

Figure 1A:
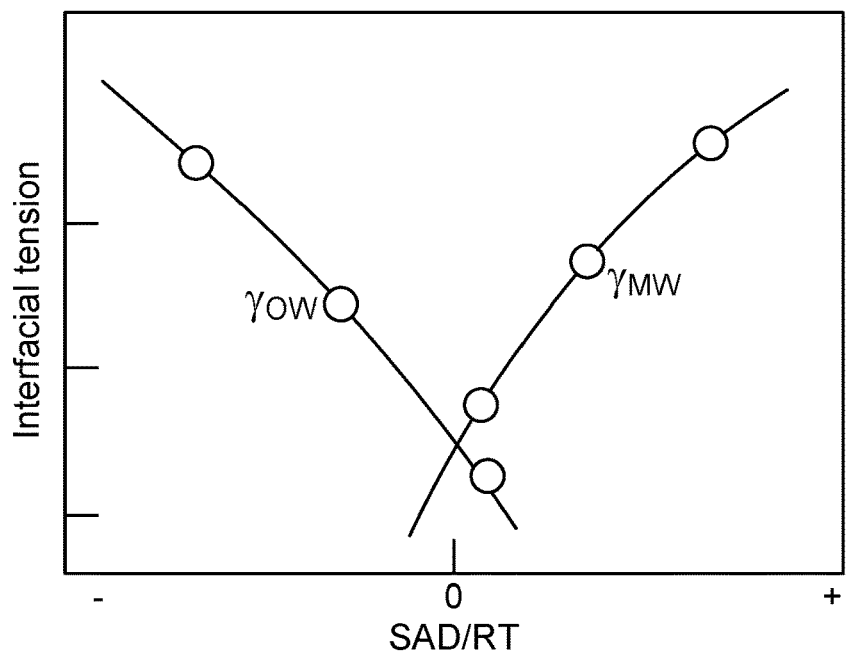
FIGS. 1A-C show the interfacial tension, the solubilization parameters, and phase behavior of a system.

Sulfuric acid alkylation involves contacting an isoalkane feed and a $C_3$-$C_5$ olefin feed with sulfuric acid in one or more reactors. The sulfuric acid catalyzes the reaction to form $C_7$-$C_9$ isoalkanes. The hydrocarbon products and unreacted hydrocarbons are separated from a sulfuric acid emulsion. The hydrocarbon portion is separated using distillation, for example, into the alkylate product, which is recovered, and unreacted isoalkane, which is recycled to the reactor. The sulfuric acid is also recycled to the reactor.

It was previously determined that surfactants, such as dioctadecyl-dimethyl-ammonium chloride (DODMAC), which form bi-continuous micro-emulsions with liquid acids and hydrocarbons, can be used in a motor fuel alkylation process, as described in U.S. application Ser. No. 16/734,475, which is incorporated herein by reference in its entirety. The process uses microheterogeneous Winsor Type III phase systems, which contain a zero-curvature bi-continuous nano-structured phase formed between oil and polar phases at surfactant addition, as a medium for "micellar catalysis" for facilitating and improvement of liquid acid catalyzed motor-fuel alkylation reaction.

A Winsor Type III micro-emulsion system is a three-phase system where a surfactant-rich middle phase co-exists with both the polar phase and oil surfactant-poor phases. The Winsor R ratio compares the tendency for an amphiphile to disperse into oil to its tendency to dissolve in water. The Winsor R ratio of cohesive energies stemming from interaction of the interfacial layer with oil divided by energies resulting from interactions with water determines the preferred interfacial curvature. A balanced interfacial layer is represented by Winsor R=1.

Alkylation processes incorporating surfactants which form a microheterogeneous Winsor Type III phase system have shown one or more of: reduced liquid acid consumption, lower acid circulation and inventory, increased reaction rate, improved alkylate octane number, and improved alkylate selectivity and yield.

Further study has led to the development of an improved sulfuric acid process utilizing surfactants and Winsor Type III systems. It has been surprisingly discovered that the optimum concentration of the surfactant depends on the olefin feed. For the linear butenes 2-butene, 1-butene, and mixtures thereof, lower concentrations of surfactant can be used to achieve the maximum benefit. For shorter chain or iso-olefins, such as propene or isobutene, higher concentrations of the surfactant are needed to provide the maximum benefit.

In addition, it has been surprisingly discovered that, in the presence of a surfactant, the concentration of sulfuric acid affects the calculated research octane number clear (RON).

Without a surfactant, the concentration of the sulfuric acid in the reaction does not significantly affect the calculated RON or yield. However, when a surfactant is included, higher concentrations of sulfuric acid resulted in higher calculated RON. The use of a surfactant and a high concentration of sulfuric acid can provide a calculated RON over 100 and close to theoretical yields. The concentration of the sulfuric acid in the catalyst is the amount of sulfuric acid divided by the total amount of sulfuric acid and water, as determined by titration with caustic and practiced by those skilled in the art.

Alkylate RON is calculated based on gas chromatography (GC) composition of $C_{5+}$ product fraction using the RON of pure compounds, but instead of assuming volumetric linear blending as taught by Chauvin (Journal of Molecular Catalysis 92 (1994) 155-165), we utilized the more accurate non-linear blending model as derived from Ghosh, Hickey, Jaffe, Development of a Detailed Gasoline Composition-Based Octane Model, Ind. Eng. Chem. Res., 2006, 45, 337-345. Accuracy is defined as result consistency with the Research Octane Number engine test as defined in ASTM D2699.

Alkylate theoretical yield is calculated by dividing the mass of alkylate produced by the mass of olefin converted. For example, theoretical mass yields for reaction of isobutane with pure propylene, butene, or pentene feed are 2.38, 2.04, and 1.83 respectively. For compositions with mixtures of C3-C5 olefins, the theoretical yield may be determined by linear combinations of these theoretical yields. Alkylate yield for a particular experiment can be determined by determining the mass of alkylate produced from GC analysis according to weighted average of carbon number divided by the mass of olefin converted during the experiment.

Likewise, a volume yield can also be calculated. The volume yield can be determined by dividing the volume of alkylate produced by the volume of olefin converted. For example, theoretical volume yields for reaction of isobutane with pure propylene, butene, or pentene feed are 1.80, 1.73, and 1.63 respectively.

The process involves selecting a $C_3$-$C_5$ olefin composition for the process. The $C_3$-$C_5$ olefin composition may comprise one or more olefins having 3, 4, or 5 carbon atoms. The olefins in the $C_3$-$C_5$ olefin composition may be linear olefins, branched olefins, or both. Linear $C_4$-$C_5$ olefins may be selected from 1-butene, 2-butene, 1-pentene, 2-pentene, and combinations thereof. Branched olefins comprise $C_3$-$C_5$ olefins not identified as linear olefins.

The concentration of sulfuric acid in an alkylation reaction zone is also selected. Increasing the concentration of the sulfuric acid used in the process results in an increase in the calculated RON.

The concentration of the surfactant is then selected based on the type of olefin composition and the sulfuric acid concentration chosen. For example, for a $C_3$-$C_5$ olefin composition comprising linear $C_4$-$C_5$ olefins, the concentration of surfactant should be greater than 0 and less than 125 ppmw based on the total reaction mixture, or less than 100 ppmw, or less than 90 ppmw, or less than 80 ppmw, or less than 70 ppmw, or less than 60 ppmw, or less than 50 ppmw, or less than 40 ppmw, or less than 30 ppmw, or less than 20 ppmw, or less than 15 ppmw, or less than 10 ppmw, or less than 5 ppmw, or a range of 5 ppmw to 125 ppmw, or 15 ppmw to 125 ppmw, or 15 ppmw to 100 ppmw, or 15 ppmw to 90 ppmw, or 15 ppmw to 80 ppmw, or 15 ppmw to 70 ppmw, or 15 ppmw to 60 ppmw, or 15 ppmw to 50 ppmw, or 15 ppmw to 40 ppmw, or 15 ppmw to 30 ppmw, or 15 ppmw to 20 ppmw, or 20 ppmw to 125 ppmw, or 20 ppmw to 100 ppmw, or 20 ppmw to 90 ppmw, or 20 ppmw to 80 ppmw, or 20 ppmw to 70 ppmw, or 20 ppmw to 60 ppmw, or 20 ppmw to 50 ppmw, or 20 ppmw to 40 ppmw, or 20 ppmw to 30 ppmw, or 30 ppmw to 125 ppmw, or 30 ppmw to 100 ppmw, or 30 ppmw to 90 ppmw, or 30 ppmw to 80 ppmw, or 30 ppmw to 70 ppmw, or 30 ppmw to 60 ppmw, or 30 ppmw to 50 ppmw, or 30 ppmw to 40 ppmw, for example.

For a $C_3$-$C_5$ olefin composition comprising branched olefins or a mixture of linear and branched olefins, the concentration of surfactant should be greater than or equal to 100 ppmw based on the total reaction mixture, or greater than or equal to 110 ppmw, or greater than or equal to 120 ppmw, or greater than or equal to 130 ppmw, or greater than or equal to 140 ppmw, or greater than or equal to 150 ppmw, or greater than or equal to 160 ppmw, or greater than or equal to 170 ppmw, or greater than or equal to 180 ppmw, or greater than or equal to 190 ppmw, or greater than or equal to 200 ppmw, or greater than or equal to 210 ppmw, or greater than or equal to 220 ppmw, or greater than or equal to 230 ppmw, or greater than or equal to 240 ppmw, or greater than or equal to 250 ppmw, or in a range of greater than or equal to 100 ppmw to 250 ppmw, or greater than or equal to 100 ppmw to 240 ppmw, or greater than or equal to 100 ppmw to 230 ppmw, or greater than or equal to 100 ppmw to 220 ppmw, or greater than or equal to 100 ppmw to 210 ppmw, or greater than or equal to 100 ppmw to 200 ppmw, or greater than or equal to 110 ppmw to 250 ppmw, or greater than or equal to 110 ppmw to 240 ppmw, or greater than or equal to 110 ppmw to 230 ppmw, or greater than or equal to 110 ppmw to 220 ppmw, or greater than or equal to 110 ppmw to 210 ppmw, or greater than or equal to 110 ppmw to 200 ppmw, or greater than or equal to 120 ppmw to 250 ppmw, or greater than or equal to 120 ppmw to 240 ppmw, or greater than or equal to 120 ppmw to 230 ppmw, or greater than or equal to 120 ppmw to 220 ppmw, or greater than or equal to 120 ppmw to 210 ppmw, or greater than or equal to 120 ppmw to 200 ppmw, or greater than or equal to 130 ppmw to 250 ppmw, or greater than or equal to 130 ppmw to 240 ppmw, or greater than or equal to 130 ppmw to 230 ppmw, or greater than or equal to 130 ppmw to 220 ppmw, or greater than or equal to 130 ppmw to 210 ppmw, or greater than or equal to 130 ppmw to 200 ppmw, or greater than or equal to 140 ppmw to 250 ppmw, or greater than or equal to 140 ppmw to 240 ppmw, or greater than or equal to 140 ppmw to 230 ppmw, or greater than or equal to 140 ppmw to 220 ppmw, or greater than or equal to 140 ppmw to 210 ppmw, or greater than or equal to 140 ppmw to 200 ppmw, or greater than or equal to 150 ppmw to 250 ppmw, or greater than or equal to 150 ppmw to 240 ppmw, or greater than or equal to 150 ppmw to 230 ppmw, or greater than or equal to 150 ppmw to 220 ppmw, or greater than or equal to 150 ppmw to 210 ppmw, or greater than or equal to 150 ppmw to 200 ppmw, or greater than or equal to 160 ppmw to 250 ppmw, or greater than or equal to 160 ppmw to 240 ppmw, or greater than or equal to 160 ppmw to 230 ppmw, or greater than or equal to 160 ppmw to 220 ppmw, or greater than or equal to 160 ppmw to 210 ppmw, or greater than or equal to 160 ppmw to 200 ppmw, or greater than or equal to 170 ppmw to 250 ppmw, or greater than or equal to 170 ppmw to 240 ppmw, or greater than or equal to 170 ppmw to 230 ppmw, or greater than or equal to 170 ppmw to 220 ppmw, or greater than or equal to 170 ppmw to 210 ppmw, or greater than or equal to 170 ppmw to 200 ppmw, or greater than or equal to 180 ppmw to 250 ppmw, or greater than or equal to 180 ppmw to 240 ppmw, or greater than or equal to 180 ppmw to 230 ppmw, or greater than or equal to 180 ppmw to 220 ppmw, or greater than or equal to 180 ppmw to 210 ppmw, or greater than or equal to 180 ppmw to 200 ppmw, or greater than or equal to 190 ppmw to 250 ppmw, or greater than or equal to 190 ppmw to 240 ppmw, or greater than or equal to 190 ppmw to 230 ppmw, or greater than or equal to 190 ppmw to 220 ppmw, or greater than or equal to 190 ppmw to 210 ppmw, or greater than or equal to 190 ppmw to 200 ppmw, or greater than or equal to 200 ppmw to 250 ppmw, or greater than or equal to 200 ppmw to 240 ppmw, or greater than or equal to 200 ppmw to 230 ppmw, or greater than or equal to 200 ppmw to 220 ppmw, or greater than or equal to 200 ppmw to 210 ppmw, or greater than or equal to 210 ppmw to 250 ppmw, or greater than or equal to 210 ppmw to 240 ppmw, or greater than or equal to 210 ppmw to 230 ppmw, or greater than or equal to 210 ppmw to 220 ppmw, or greater than or equal to 220 ppmw to 250 ppmw, or greater than or equal to 220 ppmw to 240 ppmw, or greater than or equal to 220 ppmw to 230 ppmw, or greater than or equal to 230 ppmw to 250 ppmw, or greater than or equal to 230 ppmw to 240 ppmw.

The amount of surfactant used is desirably minimized due to cost.

Figure 1B:
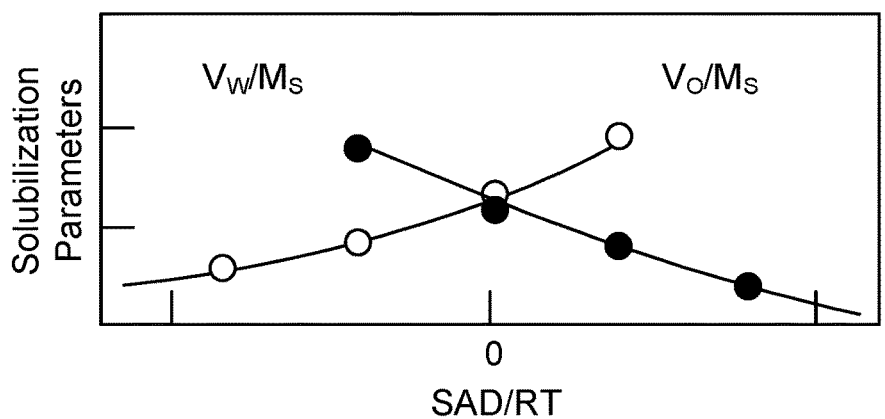
Figure 1C:
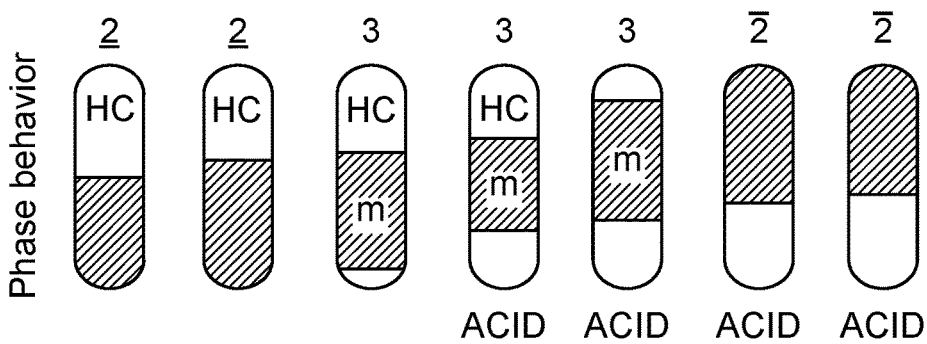
Figure 2:
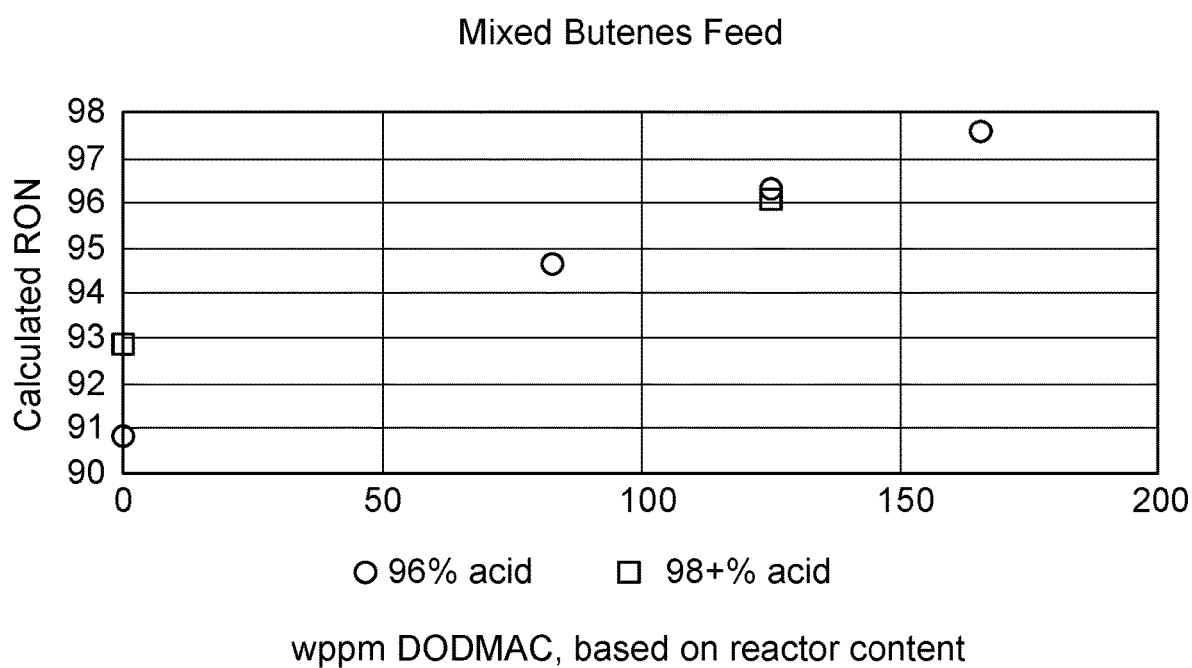
FIG. 2 is a graph showing the calculated Research Octane Number (RON) v. the amount of DODMAC surfactant for a mixed butenes feed.
Figure 3:
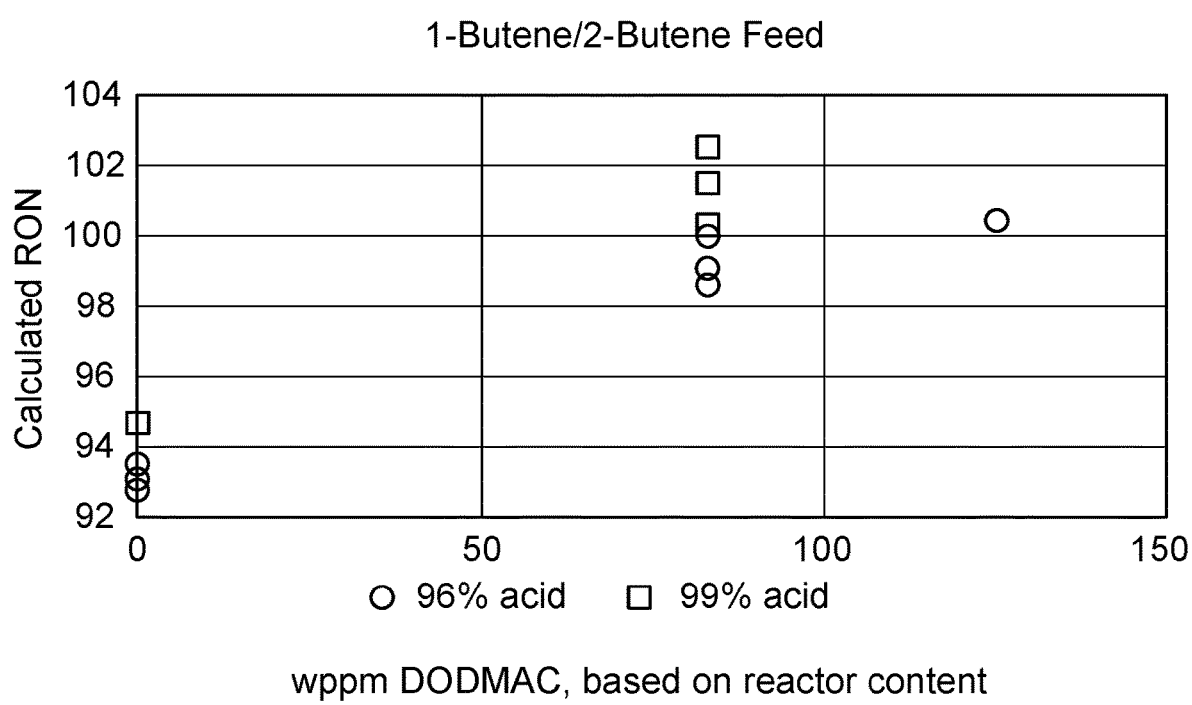
FIG. 3 is a graph showing the calculated RON v. the amount of DODMAC surfactant for a 1-butene/2-butene feed.
Figure 4:
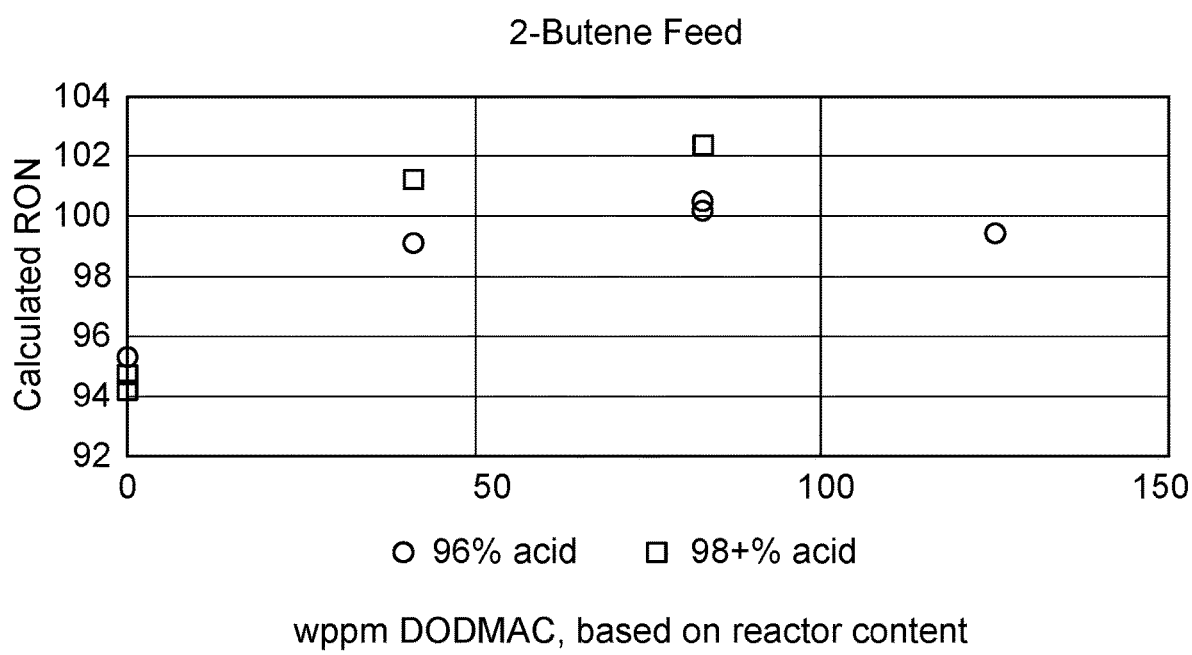
FIG. 4 is a graph showing the calculated RON v. the amount of DODMAC surfactant for a 2-butene feed.
Figure 5:
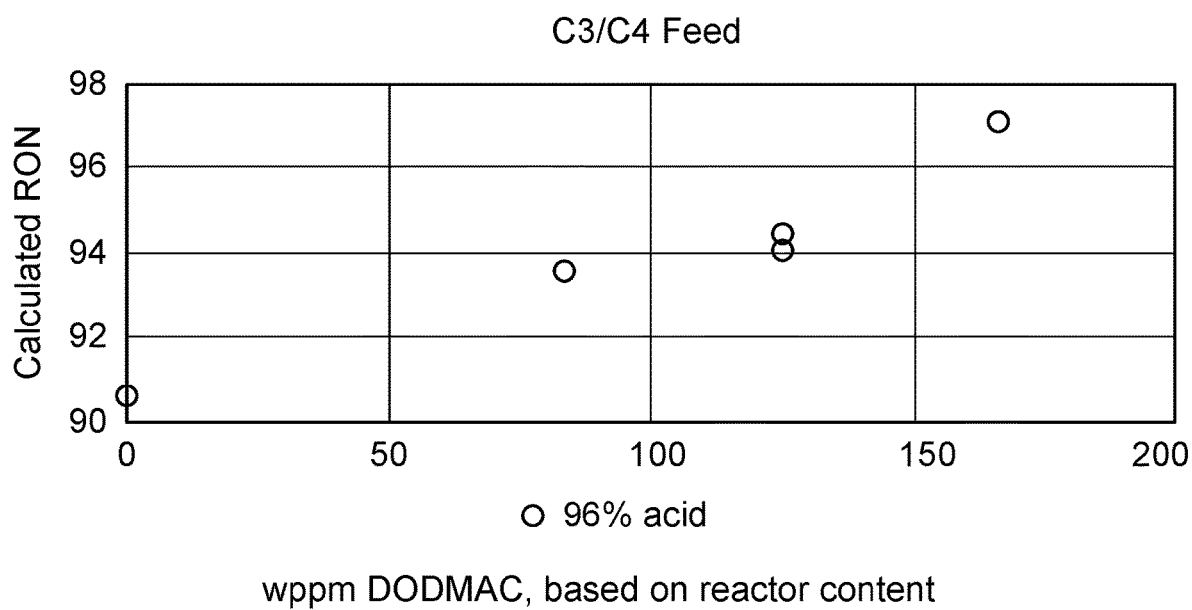
FIG. 5 is a graph showing the calculated RON v. the amount of DODMAC surfactant for a mixed $C_3/C_4$ feed.

Surfactant affinity difference (SAD) is a surfactant property in a polar/non-polar two-phase system which is responsible for how the system behaves on the addition of the surfactant. A value close to SAD/RT=0 typically means the formation of the third phase discussed above. SAD/RT can be measured as described in Salager, "The fundamental basis for the action of a chemical dehydrant. Influence of the physical and chemical formulation on the stability of an emulsion," Int'l Chem. Eng., 1990, 30, p. 103-116, which is incorporated herein by reference in its entirety. The type of emulsion can be determined in different ways. For example, the electrical conductivity can be measured. The electrical conductivity is roughly proportional to the conductivity of the external phase and the volume percent of the external phase in the emulsion. Another method involves measuring the interfacial tension. FIGS. 1A-C show the interfacial tension, the solubilization parameters, and phase behavior of a system.

Suitable surfactants for producing a Winsor Type III phase system have a solubility at 25° C. of 0.5 wt. % or less in the olefin, the isoparaffin, the sulfuric acid catalyst, and the alkylation product, or 0.4 wt % or less, or 0.3 wt % or less, or 0.2 wt % or less, or 0.1 wt % or less, or 0.09 wt % or less, or 0.08 wt % or less, or 0.07 wt % or less, or 0.06 wt % or less, or 0.05 wt % or less. The ultra-low solubility helps to reduce the amount of surfactant and liquid acid in the alkylation product after separation.

Any surfactant meeting the criteria for forming a Winsor Type III phase can be used. Suitable surfactants include, but are not limited to, a quaternary ammonium cationic salt, or a quaternary phosphonium cationic salt, or combinations thereof. Suitable quaternary ammonium cationic salts or quaternary phosphonium cationic salts include, but are not limited to, a quaternary ammonium halide, a quaternary ammonium sulfate, a quaternary ammonium hydrogen sulfate, a quaternary ammonium nitrate, a quaternary ammonium carbonate, a quaternary ammonium bicarbonate, a quaternary phosphonium halide, a quaternary phosphonium sulfate, a quaternary phosphonium hydrogen sulfate, a quaternary phosphonium nitrate, a quaternary phosphonium carbonate, a quaternary phosphonium bicarbonate, or combinations thereof.

The reaction mixture may include one or more additional components, such as antifoaming agents and the like, as would be understood by those of skill in the art.

Chemical stability of the surfactant under the reaction conditions is a desired property. Some or all of the sulfuric acid used as catalyst may be recycled to the reactor without regeneration. The surfactant may be present within the recycled sulfuric acid catalyst. Higher stability of the surfactant within the recycled sulfuric acid reduces the amount of make-up surfactant needed for the process.

The improved process uses the same equipment as the current sulfuric acid alkylation processes, making it easy to adopt in existing sulfuric acid alkylation plants. The selected olefin or olefins, isoparaffin or isoparaffins, surfactant, and sulfuric acid are introduced into a reactor. The contents are mixed ensuring contact between the olefin, isoparaffin, surfactant, and sulfuric acid, wherein the sulfuric acid catalyzes the alkylation reaction forming the alkylation product (alkylate). The reaction mixture forms the Winsor Type III phase system.

The surfactant may be added to the sulfuric acid catalyst, and the sulfuric acid catalyst/surfactant mixture can be mixed with the isoparaffin, following by mixing with the olefin. When utilizing this process in an existing plant, the point of addition of the surfactant will likely depend on the reactor system layout.

The reaction may be performed in a continuous process with one or more reactors and one or more settlers. It can also be a batch process in which the reaction and settling occur in a single vessel. In a system with more than one reactor, the surfactant can be added to one or more of the reactors.

Following the reaction, the reaction mixture is separated into a hydrocarbon phase and a sulfuric acid emulsion phase. The hydrocarbon phase comprises the alkylate product and unreacted hydrocarbon feed. The sulfuric acid emulsion phase comprises the sulfuric acid, water, and any other water soluble components. The sulfuric acid emulsion may also comprise small amounts of hydrocarbon reaction product and/or unreacted hydrocarbon feed entrained in the sulfuric acid/surfactant phase.

The separation of hydrocarbon phase from the sulfuric acid emulsion typically takes less than an hour.

The separation may take place in a settler. A settler is a vessel in which the sulfuric acid emulsion (including the surfactant) is separated from the hydrocarbons, which includes the hydrocarbon reaction product and the unreacted hydrocarbon feed. It may be an open or closed vessel. Alternatively, a centrifugal liquid-liquid separator or any mechanism that allows the acid to separate from the immiscible hydrocarbon could be used.

Separation by settling helps to minimize the amount of residual sulfur and nitrogen in the alkylate as a result of sulfuric acid emulsion carryover. The hydrocarbon phase comprises greater than 50% of the total hydrocarbon fed to the settler by volume with a sulfur content of less than 100 ppmw. The separation of hydrocarbon phase from the sulfuric acid emulsion typically takes less than an hour.

The hydrocarbon phase is then separated into alkylate and unreacted isoalkanes using known separation processes such as distillation. The alkylate is recovered, and the unreacted isoalkane is recycled to the reactor.

The bottom stream comprising the sulfuric acid emulsion may be recycled to the reactor in whole or in part. When the bottom stream is recycled to the reactor, the surfactant composition may be determined and additional surfactant added based on that determination and the $C_3$-$C_5$ olefin composition. Alternatively, or additionally, all or a portion of the bottom stream may also be sent to sulfuric acid regeneration as is known in the art.

The reaction conditions are typical reaction conditions for sulfuric acid alkylation processes. The alkylation conditions include a pressure sufficient to maintain the hydrocarbons and acid in a liquid phase, with a general range being from about 100 kPa to about 4100 kPa, or about 100 kPa to about 3100 kPa, or about 100 kPa to about 2500 kPa, or about 100 kPa to about 2100 kPa. The alkylation reaction may take place at temperatures of from −10° C. to 390° C., or −10° C. to 275° C., or −10° C. to 200° C., or −10° C. to 150° C., or −10° C. to 100° C., or −10° C. to 75° C., or −10° C. to 50° C., or −10° C. to 40° C., or −10° C. to 30° C., or −10° C. to 20° C., or 0° C. to 390° C., or 0° C. to 275° C., or 0° C. to 200° C., or 0° C. to 150° C., or 0° C. to 100° C., or 0° C. to 75° C., or 0° C. to 50° C., or 0° C. to 40° C., or 0° C. to 30° C., or 0° C. to 20° C. The reaction also occurs at liquid hourly space velocities (based on olefin content in the reaction mixture) ranging from 0.1 to 100 $hr^{-1}$, or 0.5 to 60 $hr^-$, or 1.0 to 60.0 $hr^-$, or 2.0 to 60.0 $hr^-$, or 5.0 to 60.0 $hr^-$, or 10 to 60.0 $hr^{-1}$, or 20 to 60.0 $hr^{-1}$, or 40 to 60.0 $hr^{-1}$.

In some embodiments, the conditions include a temperature of from 0° to 50° C., a pressure of from 100 kPa to 2100 kPa, and a liquid hourly space velocity of from 2.0 to 60.0 $hr^-$.

One variable in the alkylation reaction process is the molar ratio of the isoparaffin to the olefin. As known to those skilled in the art, typical alkylation zone conditions necessarily include a high ratio of the molar concentration of the isoparaffin to the molar concentration of the olefin in order to produce a high quality alkylate product. A broad range of this ratio is from about 2:1 to 20:1. For the isobutane/butene system, the isoparaffin:olefin ratio is typically in the range of 5:1 to 10:1, for example.

Another variable in the process is the volume ratio of the sulfuric acid catalyst (including the amount of sulfuric acid and water) to the hydrocarbon (including the olefin(s) and isoalkanes(s)) being fed to the alkylation reaction zone. This ratio should be minimized. A lower volume molar ratio of sulfuric acid catalyst to hydrocarbon means less sulfuric acid catalyst is required in the process. It also means that a smaller supply of sulfuric acid catalyst is needed to maintain acid inventory. By minimizing this ratio, the volume of sulfuric acid catalyst necessary is minimized, resulting in a reduction in the potential environmental and safety concerns posed by the sulfuric acid catalyst. The sulfuric acid catalyst to hydrocarbon feed volume ratio may vary from 0.005:1 to 100:1, or 0.005:1 to 80:1, or 0.005:1 to 60:1, or 0.005:1 to 40:1, or 0.005:1 to 30:1, or 0.005:1 to 25:1, or 0.005:1 to 20:1, or 0.005:1 to 10:1, or 0.01:1 to 100:1, or 0.01:1 to 80:1, or 0.01:1 to 60:1, or 0.01:1 to 40:1, or 0.01:1 to 30:1, or 0.01:1 to 25:1, or 0.01:1 to 20:1, or 0.01:1 to 10:1, or 0.1:1 to 100:1, or 0.1:1 to 80:1, or 0.1:1 to 60:1, or 0.1:1 to 40:1, or 0.1:1 to 30:1, or 0.1:1 to 25:1, or 0.1:1 to 20:1, or 0.1:1 to 10:1, or 1:1 to 100:1, or 1:1 to 80:1, or 1:1 to 60:1, or 1:1 to 40:1, or 1:1 to 30:1, or 1:1 to 25:1, or 1:1 to 20:1, or 1:1 to 10:1.

The concentration of the sulfuric acid can be any suitable concentration for accomplishing the alkylation reaction. Suitable concentrations include, but are not limited to greater than 95%, or greater than 96%, or greater than 97%, or greater than 98%, or greater than 99%. As appreciated by those skilled in the art, chemical grade sulfuric acid can be reacted with oleum to achieve sulfuric acid concentrations greater than what can be purchased from chemical vendors.

Reaction zone conditions for the production of a motor fuel alkylate from a $C_3$ to $C_5$ olefin, an isoparaffin, and a sulfuric acid catalyst can include a temperature of from 0° C. to 50° C., a pressure of from 100 to 2100 kPa, and a liquid hourly space velocity of from 2 to 60 $hr^-$. The sulfuric acid catalyst to C3-C5 olefin volume feed ratio can be in the range from 100:1 to 1:200, or 100:1 to 1:150, or 100:1 to 1:100, or 100:1 to 1:75, or 100:1 to 1:50, or 80:1 to 1:200, or 80:1 to 1:150, or 80:1 to 1:100, or 80:1 to 1:75, or 80:1 to 1:50, or 60:1 to 1:200, or 60:1 to 1:150, or 60:1 to 1:100, or 60:1 to 1:75, or 60:1 to 1:50, or 50:1 to 1:200, or 50:1 to 1:150, or 50:1 to 1:100, or 50:1 to 1:75, or 50:1 to 1:50, or 40:1 to 1:200, or 40:1 to 1:150, or 40:1 to 1:100, or 40:1 to 1:75, or 40:1 to 1:50, or 30:1 to 1:200, or 30:1 to 1:150, or 30:1 to 1:100, or 30:1 to 1:75, or 30:1 to 1:50, or 20:1 to 1:200, or 20:1 to 1:150, or 20:1 to 1:100, or 20:1 to 1:75, or 20:1 to 1:50.

One aspect of the invention is a process for sulfuric acid catalyzed alkylation. In one embodiment, the process comprises: selecting a $C_3$-$C_5$ olefin composition; selecting a concentration of a surfactant based on the $C_3$-$C_5$ olefin composition selected; and reacting the $C_3$-$C_5$ olefin composition and an isoparaffin in the presence of a sulfuric acid catalyst and the surfactant in the alkylation reaction zone operating at alkylation reaction conditions to form a reaction mixture comprising an alkylation product, the reaction mixture comprising a Winsor Type III phase system, wherein the surfactant has a solubility at 25° C. of 0.5% or less in the $C_3$-$C_5$ olefin composition, the isoparaffin, the sulfuric acid catalyst, and the alkylation product, and wherein a calculated RON of the alkylation product is greater than a calculated RON of an alkylation product reacted in the absence of the surfactant.

In some embodiments, when the $C_3$-$C_5$ olefin composition comprises a linear $C_4$-$C_5$ olefin, the concentration of the surfactant is less than 100 ppmw and greater than 15 ppmw of the reaction mixture.

In some embodiments, the linear $C_3$-$C_5$ olefin composition comprises 1-butene, 2-butene, or combinations thereof.

In some embodiments, the concentration of the surfactant is less than 90 ppmw of the reaction mixture.

In some embodiments, when the $C_3$-$C_5$ olefin composition comprises a branched olefin or a mixture of linear olefins and branched olefins, the concentration of the surfactant is greater than or equal to 100 ppmw and less than 250 ppmw of the reaction mixture.

In some embodiments, the branched olefin comprises isobutene or wherein the mixture of linear and branched olefins comprises a mixture of $C_3$ and $C_4$ olefins.

In some embodiments, the mixture of linear and branched olefins comprises a mixture of isobutene, 1-butene, and 2-butene.

In some embodiments, the concentration of the surfactant is greater than or equal to 120 ppmw of the reaction mixture.

In some embodiments, the isoparaffin comprises isobutane, isopentane, or combinations thereof.

In some embodiments, the surfactant comprises a quaternary ammonium cationic salt, or a quaternary phosphonium cationic salt, or combinations thereof.

In some embodiments, the quaternary ammonium cationic salt or a quaternary phosphonium cationic salt comprises a quaternary ammonium halide, a quaternary ammonium sulfate, a quaternary ammonium hydrogen sulfate, a quaternary ammonium nitrate, a quaternary ammonium carbonate, a quaternary ammonium bicarbonate, a quaternary phosphonium halide, a quaternary phosphonium sulfate, a quaternary phosphonium hydrogen sulfate, a quaternary phosphonium nitrate, a quaternary phosphonium carbonate, a quaternary phosphonium bicarbonate, or combinations thereof.

Suitable quaternary ammonium halides include, but are not limited to, quaternary ammonium chlorides, quaternary ammonium bromides, quaternary ammonium iodides, and quaternary ammonium fluorides.

In some embodiments, the surfactant comprises dibutyl dioctyldecyl ammonium chloride, dimethyl dipentadecyl ammonium chloride, diethyl dipentadecyl ammonium chloride, dipropyl dipentadecyl ammonium chloride, dibutyl dipentadecyl ammonium chloride, dimethyl dihexadecyl ammonium chloride, diethyl dihexadecyl ammonium chloride, dipropyl dihexadecyl ammonium chloride, dibutyl dihexadecyl ammonium chloride, dimethyl diheptadecyl ammonium chloride, diethyl diheptadecyl ammonium chloride, dipropyl diheptadecyl ammonium chloride, dibutyl diheptadecyl ammonium chloride, dimethyl dioctadecyl ammonium chloride, diethyl dioctadecyl ammonium chloride, dipropyl dioctadecyl ammonium chloride, dimethyl dinonadecyl ammonium chloride, diethyl dinonadecyl ammonium chloride, dipropyl dinonadecyl ammonium chloride, dibutyl dinonadecyl ammonium chloride, dimethyl diicosylecyl ammonium chloride, diethyl diicosyldecyl ammonium chloride, dipropyl diicosyldecyl ammonium chloride, dibutyl diicosyldecyl ammonium chloride, or combinations thereof. Bromide, iodide, and fluoride analogues could also be used.

In some embodiments, the process further comprising: separating the alkylation product from the reaction mixture.

In some embodiments, the alkylation reaction conditions include at least one of: a temperature of from −10° to 50° C., a pressure of from 100 kPa to 2100 kPa, or a liquid hourly space velocity of from 0.1 to 60.0 hr⁻.

In some embodiments, the alkylation reaction conditions include at least one of: a temperature of from 0° to 50° C., a pressure of from 100 kPa to 2100 kPa, or a liquid hourly space velocity of from 0.5 to 60.0 hr⁻.

In some embodiments, the process further comprises: increasing a concentration of the sulfuric acid catalyst from a first concentration to a second concentration, and wherein a calculated RON of the alkylation product at the second concentration of the sulfuric acid catalyst is greater than a calculated RON of the alkylation product at the first concentration of the sulfuric acid catalyst.

In some embodiments, the calculated RON of the alkylation product is greater than 100. In some embodiments, the calculated RON of the alkylation product is at least 1 calculated RON number greater than the calculated RON in the absence of the surfactant, or at least 2 calculated RON numbers greater, or at least 3 calculated RON numbers greater, or at least 4 calculated RON numbers greater, or at least 5 calculated RON numbers greater. For example, the average improvement in calculated RON for a propylene feed may be about 1. For a mixed butenes feed, it may be about 2, for normal butenes, it may be about 3, and for a 2-butenes feed, it may be about 3 to 4.

In some embodiments, the process further comprises: increasing a concentration of the sulfuric acid catalyst from a first concentration to a second concentration, and wherein a calculated RON of the alkylation product at the second concentration of the sulfuric acid catalyst is greater than a calculated RON of the alkylation product at the first concentration of the sulfuric acid catalyst.

In some embodiments, when the $C_3$-$C_5$ olefin composition comprises the mixture of linear and branched olefins, selecting the concentration of the surfactant comprises selecting the concentration based on a relative ratio of the $C_3$-$C_5$ olefins selected.

One aspect of the invention is a process for sulfuric acid catalyzed alkylation. In one embodiment, the process comprises: selecting a $C_3$-$C_5$ olefin composition; selecting a concentration of sulfuric acid in an alkylation reaction zone; selecting a concentration of a surfactant based on the $C_3$-$C_5$ olefin composition selected and the sulfuric acid concentration selected; reacting the $C_3$-$C_5$ olefin composition and an isoparaffin in the presence of a sulfuric acid catalyst and the surfactant in the alkylation reaction zone operating at alkylation reaction conditions to form a reaction mixture comprising an alkylation product, the reaction mixture comprising a Winsor Type III phase system, wherein the surfactant has a solubility at 25° C. of 0.5% or less in the $C_3$-$C_5$ olefin composition, the isoparaffin, the sulfuric acid catalyst, and the alkylation product, and wherein a calculated RON of the alkylation product is greater than a calculated RON of an alkylation product reacted in the absence of the surfactant; and separating the alkylation product from the reaction mixture.

Another aspect of the invention is a process for sulfuric acid catalyzed alkylation. In one embodiment, the process comprises: selecting a $C_3$-$C_5$ olefin composition; selecting a concentration of a surfactant based on the $C_3$-$C_5$ olefin composition selected, wherein the surfactant comprises dioctadecyl-dimethyl-ammonium halide; reacting the $C_3$-$C_5$ olefin composition and an isoparaffin in the presence of a sulfuric acid catalyst and the surfactant in an alkylation reaction zone operating at alkylation reaction conditions to form a reaction mixture comprising an alkylation product, the reaction mixture comprising a Winsor Type III phase system, wherein the surfactant has a solubility at 25° C. of 0.5% or less in the $C_3$-$C_5$ olefin composition, the isoparaffin, the sulfuric acid catalyst, and the alkylation product, and wherein a calculated RON of the alkylation product is greater than a calculated RON of an alkylation product reacted in the absence of the surfactant; separating the reaction mixture into a hydrocarbon stream comprising the alkylation product and a bottom stream comprising an emulsion comprising sulfuric acid and the surfactant; separating the hydrocarbon stream into an alkylation product stream and a recycle stream comprising at least one of unreacted isoparaffin and unreacted olefin; recovering the alkylation product stream; and optionally recycling the recycle stream to the alkylation reaction zone; wherein when the $C_3$-$C_5$ olefin composition comprises a linear $C_3$-$C_5$ olefin, the concentration of the surfactant is less than 100 ppmw of the reaction mixture; and when the $C_3$-$C_5$ olefin composition comprises a branched olefin or a mixture of linear and branched olefins, the concentration of the surfactant is greater than or equal to 100 ppmw of the reaction mixture.

In some embodiments, the process further comprises: increasing a concentration of the sulfuric acid catalyst from a first concentration to a second concentration, and wherein a calculated RON of the alkylation product at the second concentration of the sulfuric acid catalyst is greater than a calculated RON of the alkylation product at the first concentration of the sulfuric acid catalyst.

As used herein, the term "zone" can refer to an area including one or more equipment items as appropriate for the type of zone and/or one or more sub-zones or sub-sections. Equipment items can include, but are not limited to, one or more reactors or reactor vessels, separation vessels, adsorbent chamber or chambers, distillation towers, heaters, exchangers, pipes, pumps, compressors, and controllers. Additionally, an equipment item, such as a reactor, dryer, adsorbent chamber or vessel, can further include one or more sections, sub-sections, zones, or sub-zones.

EXAMPLES

Experiments were conducted to demonstrate and evaluate the invention.

Comparative Example 1A

A pre-dried 300 mL autoclave containing impellers optimized for the reactor geometry was charged with 183 g of 96% $H_2SO_4$ followed by 53 g of isobutane. After cooling the reactor to about 3° C., about 5 g of mixed butenes was added to the reactor via syringe pump for the duration of 14 minutes. Mixing was maintained at 750 rpm for the duration of olefin addition. The reactor contents were then transferred to a Fisher-Porter bottle for settling. The hydrocarbon phase was routed to a gas chromatograph (GC) with flame ionization (FID) detector for product analysis. Example 1A showed a calculated RON of 91 and $C_{9+}$ selectivity of 34% wt.

Example 1B: The experiment was carried out as described in Example 1A where 98% $H_2SO_4$ was used instead. The calculated RON was 93, and $C_{9+}$ selectivity was 23% wt.

Example 1C: The experiment was carried out as described in Example 1A where 0.02 g of DODMAC was dissolved in the $H_2SO_4$ prior to carrying out the alkylation reaction. The calculated RON was 95, and $C_{9+}$ selectivity was 19% wt.

Example 1D: The experiment was carried out as described in Example 1A where 0.03 g of DODMAC was dissolved in the $H_2SO_4$ prior to carrying out the alkylation reaction. The calculated RON was 96, and $C_{9+}$ selectivity was 15% wt.

Example 1E: The experiment was carried out as described in Example 1A where 0.03 g of DODMAC was dissolved in 98% $H_2SO_4$ prior to carrying out the alkylation reaction. The calculated RON was 96, and $C_{9+}$ selectivity was 16% wt.

Example 1F: The experiment was carried out as described in Example 1A where 0.04 g of DODMAC was dissolved in $H_2SO_4$ prior to carrying out the alkylation reaction. The calculated RON was 98 and $C_{9+}$ selectivity was 10% wt.

The results are summarized in Table 1. I/O mol actual is the actual isoparaffin to olefin molar ratio. C/O wt actual is the actual mass of sulfuric acid (catalyst) tested divided by the cumulative mass of olefins added during the experiment.

For both 96% and 98% $H_2SO_4$, an increase in calculated RON and decrease in $C_{9+}$ selectivity was observed with increasing amounts of DODMAC.

TABLE 1

| MIXED BUTENES FEED (39% wt isobutylene, 33% wt 2-butenes, 28% wt 1-butenes) | Example 1A | Example 1B | Example 1C | Example 1D | Example 1E | Example 1F |
|---|---|---|---|---|---|---|
| H2SO4 Purity | 96% | 98% | 96% | 96% | 98% | 96% |
| g DODMAC | 0 | 0 | 0.02 | 0.03 | 0.03 | 0.04 |
| wppm DODMAC, based on reactor contents | 0 | 0 | 83 | 125 | 125 | 166 |
| % cum. olefin conv. | 99 | 100 | 100 | 100 | 100 | 100 |
| I/O mol actual | 9.8 | 8.9 | 8.8 | 10.1 | 9.8 | 8.7 |
| C/O wt actual | 35.0 | 31.5 | 31.5 | 36.0 | 35.0 | 30.9 |
| LHSV, hr$^{-1}$ | 0.38 | 0.42 | 0.42 | 0.37 | 0.38 | 0.43 |
| C5+ Yield | 1.47 | 1.82 | 1.69 | 2.25 | 2.02 | 2.32 |
| C5+ wt % | 12.96 | 17.76 | 16.55 | 19.61 | 18.02 | 23.12 |
| C9+ wt % Sel. | 34 | 23 | 19 | 15 | 16 | 10 |
| Calculated RON | 91 | 93 | 95 | 96 | 96 | 98 |

Examples 2A through 2K: The experiments were carried out as described in Example 1A where variable amounts of DODMAC were dissolved in 96% or 99% $H_2SO_4$ prior to carrying out the alkylation reaction. The olefin feed was a blend of linear 1-butenes and 2-butenes. Specific experimental conditions and alkylate quality results are summarized in Table 2.

On average, alkylate calculated RON was improved by about 3 numbers for each 0.01 g increment of DODMAC added compared to no DODMAC case for each acid concentration.

Examples 3A through 3K: The experiments were carried out as described in Example 1A where variable amounts of DODMAC were dissolved in 96%, 98%, or 99+% $H_2SO_4$ prior to carrying out the alkylation reaction. The olefin feed was 2-butenes. In Example 3L, dioctadecyl-dimethyl-ammonium bromide (DODMAB) was used instead of DODMAC. Specific experimental conditions and alkylate quality results are summarized in Table 3.

On average, alkylate calculated RON was improved by about 3 to 4 numbers for each 0.01 g increment of DODMAC added compared to no DODMAC case for each acid concentration.

TABLE 2

| LINEAR BUTENES (30% 1-butene, 70% 2-butenes) | Example 2A | Example 2B | Example 2C | Example 2D | Example 2E | Example 2F | Example 2G | Example 2H | Example 2I | Example 2J | Example 2K |
|---|---|---|---|---|---|---|---|---|---|---|---|
| H2SO4 Purity | 96% | 96% | 96% | 99% | 96% | 96% | 96% | 99% | 99% | 99% | 96% |
| g DODMAC | 0 | 0 | 0 | 0 | 0.02 | 0.02 | 0.02 | 0.02 | 0.02 | 0.02 | 0.03 |
| wppm DODMAC, based on reactor contents | 0 | 0 | 0 | 0 | 83 | 83 | 83 | 83 | 83 | 83 | 125 |
| % cum. olefin conv. | 100 | 94 | 97 | 98 | 100 | 99 | 100 | 100 | 100 | 100 | 100 |
| I/O mol actual | 9.0 | 9.3 | 10.0 | 8.7 | 8.5 | 9.5 | 10.0 | 9.1 | 10.3 | 9.3 | 9.9 |
| C/O wt actual | 32.1 | 33.1 | 35.6 | 31.1 | 30.4 | 34.0 | 35.9 | 32.6 | 36.9 | 33.4 | 35.5 |
| LHSV, hr$^{-1}$ | 0.41 | 0.40 | 0.37 | 0.42 | 0.43 | 0.39 | 0.37 | 0.40 | 0.36 | 0.39 | 0.37 |
| C5+ Yield | 1.34 | 1.50 | 1.58 | 1.78 | 1.32 | 1.67 | 2.11 | 2.13 | 1.79 | 2.13 | 1.92 |
| C5+ wt % | 12.84 | 13.09 | 13.37 | 17.23 | 13.21 | 15.14 | 18.34 | 20.22 | 15.15 | 19.74 | 16.91 |
| C9+ Sel. | 28 | 29 | 28 | 20 | 7 | 9 | 7 | 3 | 7 | 3 | 5 |
| Calculated RON | 93 | 93 | 93 | 95 | 100 | 99 | 99 | 102 | 100 | 101 | 100 |

TABLE 3

| 2-BUTENES FEED (60% trans-2-butenes/40% cis-2butenes) | Example 3A | Example 3B | Example 3C | Example 3D | Example 3E | Example 3F | Example 3G | Example 3H | Example 3I | Example 3J | Example 3K | Example 3L |
|---|---|---|---|---|---|---|---|---|---|---|---|---|
| H2SO4 Purity | 96% | 96% | 98% | 99+% | 96% | 98% | 96% | 96% | 99+% | 99+% | 96% | 96% |
| g DODMAC | 0 | 0 | 0 | 0 | 0.01 | 0.01 | 0.02 | 0.02 | 0.02 | 0.02 | 0.03 | 0.02* |
| wppm DODMAC, based on reactor contents | 0 | 0 | 0 | 0 | 41 | 41 | 83 | 83 | 83 | 83 | 125 | 83 |
| % cum. olefin conv. | 100 | 100 | 100 | 99 | 100 | 99 | 100 | 100 | 100 | 100 | 100 | 97 |
| I/O mol actual | 8.8 | 10.8 | 10.7 | 9.8 | 9.0 | 10.4 | 8.4 | 8.9 | 10.6 | 11.4 | 9.3 | 9.8 |
| C/O wt actual | 31.5 | 38.6 | 38.2 | 35.0 | 32.3 | 37.0 | 30.1 | 31.8 | 37.6 | 40.7 | 33.8 | 35.2 |
| LHSV, hr$^{-1}$ | 0.42 | 0.34 | 0.34 | 0.38 | 0.41 | 0.35 | 0.44 | 0.41 | 0.35 | 0.32 | 0.39 | 0.37 |
| C5+ Yield | 1.74 | 1.55 | 1.49 | 1.41 | 1.44 | 1.42 | 1.92 | 1.71 | 2.05 | 2.01 | 2.14 | 1.72 |
| C5+ wt % | 16.94 | 12.53 | 12.14 | 12.35 | 13.85 | 11.90 | 19.67 | 16.48 | 16.99 | 15.51 | 19.32 | 14.65 |
| C9+ Sel. | 23 | 25 | 25 | 24 | 8 | 5 | 4 | 5 | 1 | 1 | 4 | 10 |
| Calculated RON | 95 | 95 | 94 | 95 | 99 | 101 | 100 | 100 | 102 | 102 | 99 | 98 |

*DODMAB loading instead of DODMAC

Examples 4A through 4E: The experiments were carried out as described in Example 1A where variable amounts of DODMAC were dissolved in 96% H₂SO₄ prior to carrying out the alkylation reaction. The olefin feed was a blend of propylene and mixed butenes. Specific experimental conditions and alkylate quality results are summarized in Table 4.

On average, alkylate calculated RON was improved by about 1 number for each 0.01 g increment of DODMAC added compared to no DODMAC case.

TABLE 4

| PROPYLENE FEED (33% wt C3=, 25% wt 2-butenes, 18% wt 1-butenes, 24% wt isobutylene) | Example 4A | Example 4B | Example 4C | Example 4D | Example 4E |
|---|---|---|---|---|---|
| H2SO4 Purity | 96% | 96% | 96% | 96% | 96% |
| g DODMAC | 0 | 0.02 | 0.03 | 0.03 | 0.04 |
| wppm DODMAC, based on reactor contents | 0 | 83 | 125 | 125 | 166 |
| % cum. olefin conv. | 96 | 99 | 99 | 98 | 98 |
| I/O mol actual | 10.3 | 8.8 | 8.1 | 10.8 | 10.3 |
| C/O wt actual | 36.8 | 31.5 | 28.8 | 38.8 | 36.7 |
| LHSV, hr$^{-1}$ | 0.36 | 0.42 | 0.46 | 0.34 | 0.36 |
| C5+ Yield | 1.53 | 1.18 | 1.28 | 1.41 | 1.98 |
| C5+ wt % | 12.32 | 11.50 | 13.39 | 11.16 | 16.52 |
| C9+ wt % Sel. | 33 | 22 | 21 | 17 | 10 |
| Calculated RON | 91 | 94 | 94 | 94 | 97 |

Examples 5A to 5E: The experiments were carried out similar to what is described in Example 1A where variable amounts of DODMAC, I/O ratios, and reaction temperatures were tested as specified in Table 5.

TABLE 5

| 2-BUTENES FEED (60% trans-2-butenes/40% cis-2butenes) - Temperature Effects | Example 5A | Example 5B | Example 5C | Example 5D | Example 5E |
|---|---|---|---|---|---|
| Temperature, °C. | 4 | 22 | -3 | 3 | 24 |
| H2SO4 Purity | 96% | 96% | 96% | 96% | 96% |
| g DODMAC | 0 | 0 | 0.02 | 0.02 | 0.02 |
| wppm DODMAC, based on reactor contents | 0 | 0 | 83 | 83 | 83 |
| % cum. olefin conv. | 100 | 100 | 100 | 100 | 100 |
| I/O mol actual | 8.8 | 7.9 | 5.5 | 8.4 | 8.4 |
| C/O wt actual | 31.5 | 28.3 | 19.8 | 30.1 | 29.9 |
| LHSV, hr$^{-1}$ | 0.42 | 0.46 | 0.66 | 0.44 | 0.44 |
| C5+ Yield | 1.74 | 1.87 | 1.91 | 1.92 | 2.04 |
| C5+ wt % | 16.94 | 20.03 | 27.76 | 19.67 | 20.90 |
| C9+ Sel | 23 | 16 | 22 | 4 | 3 |
| Calculated RON | 95 | 94 | 93 | 100 | 97 |

Examples 6A to 6E: The experiments were carried similar to what is described in Example 1A where variable amounts of DODMAC and 2-butenes addition rate were varied to achieve the LHSV indicated in Table 6.

With increased LHSV, alkylate calculated RON decreases but in the presence of DODMAC, the calculated RON debit is less.

TABLE 6

| 2-BUTENES FEED (60% trans-2-butenes/40% cis-2butenes) - Space Velocity Effects @ 3C | Example 6A | Example 6B | Example 6C | Example 6D |
|---|---|---|---|---|
| LHSV, hr$^{-1}$ | 0.42 | 0.44 | 1.09 | 1.13 |
| H2SO4 Purity | 96% | 96% | 96% | 96% |
| g DODMAC | 0 | 0.02 | 0 | 0.02 |
| wppm DODMAC, based on reactor contents | 0 | 83 | 0 | 83 |
| % cum. olefin conv. | 100 | 100 | 100 | 100 |
| I/O mol actual | 8.8 | 8.4 | 7.4 | 7.2 |
| C/O wt actual | 31.5 | 30.1 | 26.4 | 25.4 |
| C5+ Yield | 1.74 | 1.92 | 1.38 | 1.52 |
| C5+ wt % | 16.94 | 19.67 | 15.60 | 17.77 |
| C9+ Sel | 23 | 5 | 35 | 11 |
| Calculated RON | 95 | 100 | 87 | 97 |

Examples 7A to 7D: The sulfuric acid and isobutane loadings were varied such to achieve the acid to hydrocarbon volume ratios indicated in Table 7.

With reduced acid volume fraction it was noted that the selectivity to $C_{9+}$ increases, but with DODMAC the amount of $C_{9+}$ products is reduced and alkylate yield is improved.

TABLE 7

| 2-BUTENES FEED (60% trans-2-butenes/ 40% cis-2butenes) - Volume Fraction Study @ 3C | Example 7A | Example 7B | Example 7C | Example 7D |
|---|---|---|---|---|
| H2SO4 Purity | 96% | 96% | 96% | 96% |
| g DODMAC | 0 | 0 | 0.02 | 0.02 |
| wppm DODMAC, based on reactor contents | 0 | 0 | 83 | 110 |
| H2SO4: Hydrocarbon, volume | 1 | 0.5 | 1 | 0.5 |
| % cum. olefin conv. | 100 | 100 | 100 | 100 |
| I/O mol actual | 8.8 | 9.5 | 8.4 | 9.7 |
| C/O wt actual | 31.5 | 11.0 | 30.1 | 11.2 |
| C5+ Yield | 1.74 | 1.73 | 1.92 | 2.08 |
| C5+ wt % | 16.94 | 15.81 | 19.67 | 18.66 |
| C9+ Sel | 23 | 29 | 4 | 15 |
| Calculated RON | 95 | 94 | 100 | 95 |
| LHSV, hr$^{-1}$ | 0.42 | 1.19 | 0.44 | 1.17 |

As shown in Table 8, higher strength acid affects a change in the selectivity of alkylate trimethylpentanes, but the overall selectivity to C8s is unaltered. In the presence of DODMAC, not only are more C8s produced, but the amount of trimethylpentanes also increased resulting in a significance enhancement of the alkylate calculated RON produced.

TABLE 8

| Species (mol % selectivity) | $H_2SO_4$ | | $H_2SO_4$ + 83 ppm DODMAC | |
|---|---|---|---|---|
| | 96.7% | 99.6% | 96.7% | 99.6% |
| 223TMP | 1.4 | 2.9 | 2.4 | 2.9 |
| 224TMP | 20.7 | 27.8 | 30.5 | 38.4 |
| 233TMP | 14.5 | 11.9 | 23.8 | 26.6 |
| 234TMP | 13.0 | 7.6 | 22.3 | 22.5 |
| Total C8 | 57.3 | 57.9 | 87.0 | 95.6 |
| TMP/DMH | 6.9 | 6.9 | 11.5 | 18.1 |
| Yield (g/g $C_4^=$) | 1.5 | 1.5 | 1.9 | 2.0 |
| RON | 96.4 | 96.6 | 99.7 | 102.3 |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

Specific Embodiments

While the following is described in conjunction with specific embodiments, it will be understood that this description is intended to illustrate and not limit the scope of the preceding description and the appended claims.

A first embodiment of the invention is a process for sulfuric acid catalyzed alkylation comprising selecting a $C_3$-$C_5$ olefin composition; selecting a concentration of a surfactant based on the $C_3$-$C_5$ olefin composition selected; reacting the $C_3$-$C_5$ olefin composition and an isoparaffin in the presence of a sulfuric acid catalyst and the surfactant in the alkylation reaction zone operating at alkylation reaction conditions to form a reaction mixture comprising an alkylation product, the reaction mixture comprising a Winsor Type III phase system, wherein the surfactant has a solubility at 25° C. of 0.5% or less in the $C_3$-$C_5$ olefin composition, the isoparaffin, the sulfuric acid catalyst, and the alkylation product, and wherein a calculated RON of the alkylation product is greater than a calculated RON of an alkylation product reacted in the absence of the surfactant. An embodiment of the invention is one, any or all of prior embodiments in this paragraph up through the first embodiment in this paragraph wherein when the $C_3$-$C_5$ olefin composition comprises a linear $C_4$-$C_5$ olefin, the concentration of the surfactant is less than 100 ppmw of the reaction mixture. An embodiment of the invention is one, any or all of prior embodiments in this paragraph up through the first embodiment in this paragraph wherein the linear $C_4$-$C_5$ olefin comprises 1-butene, 2-butene, or combinations thereof. An embodiment of the invention is one, any or all of prior embodiments in this paragraph up through the first embodiment in this paragraph wherein the concentration of the surfactant is less than 90 ppmw of the reaction mixture. An embodiment of the invention is one, any or all of prior embodiments in this paragraph up through the first embodiment in this paragraph wherein when the $C_3$-$C_5$ olefin composition comprises a branched olefin or a mixture of linear and branched olefins, the concentration of the surfactant is greater than or equal to 100 ppmw of the reaction mixture. An embodiment of the invention is one, any or all of prior embodiments in this paragraph up through the first embodiment in this paragraph wherein the branched olefins comprise isobutene, or wherein the mixture of linear and branched olefins comprises a mixture of $C_3$ and $C_4$ olefins. An embodiment of the invention is one, any or all of prior embodiments in this paragraph up through the first embodiment in this paragraph wherein the mixture of linear and branched olefins comprises a mixture of isobutene, 1-butene, and 2-butene. An embodiment of the invention is one, any or all of prior embodiments in this paragraph up through the first embodiment in this paragraph wherein the concentration of the surfactant is greater than or equal to 120 ppmw of the reaction mixture. An embodiment of the invention is one, any or all of prior embodiments in this paragraph up through the first embodiment in this paragraph wherein the isoparaffin comprises isobutane, isopentane, or combinations thereof. An embodiment of the invention is one, any or all of prior embodiments in this paragraph up through the first embodiment in this paragraph wherein the surfactant comprises a quaternary ammonium cationic salt, or a quaternary phosphonium cationic salt, or combinations thereof. An embodiment of the invention is one, any or all of prior embodiments in this paragraph up through the first embodiment in this paragraph wherein the quaternary ammonium cationic salt or a quaternary phosphonium cationic salt comprises a quaternary ammonium halide, a quaternary ammonium sulfate, a quaternary ammonium hydrogen sulfate, a quaternary ammonium nitrate, a quaternary ammonium carbonate, a quaternary ammonium bicarbonate, a quaternary phosphonium halide, a quaternary phosphonium sulfate, a quaternary phosphonium hydrogen sulfate, a quaternary phosphonium nitrate, a quaternary phosphonium carbonate, a quaternary phosphonium bicarbonate, or combinations thereof. An embodiment of the invention is one, any or all of prior embodiments in this paragraph up through the first embodiment in this paragraph wherein the surfactant comprises dibutyl dioctyldecyl ammonium chloride, dimethyl dipentadecyl ammonium chloride, diethyl dipentadecyl ammonium chloride, dipropyl dipentadecyl ammonium chloride, dibutyl dipentadecyl ammonium chloride, dimethyl dihexadecyl ammonium chloride, diethyl dihexadecyl ammonium chloride, dipropyl dihexadecyl ammonium chloride, dibutyl dihexadecyl ammonium chloride, dimethyl diheptadecyl ammonium chloride, diethyl diheptadecyl ammonium chloride, dipropyl diheptadecyl ammonium chloride, dibutyl diheptadecyl ammonium chloride, dimethyl dioctadecyl ammonium chloride, diethyl dioctadecyl ammonium chloride, dipropyl dioctadecyl ammonium chloride, dimethyl dinonadecyl ammonium chloride, diethyl dinonadecyl ammonium chloride, dipropyl dinonadecyl ammonium chloride, dibutyl dinonadecyl ammonium chloride, dimethyl diicosylecyl ammonium chloride, diethyl diicosyldecyl ammonium chloride, dipropyl diicosyldecyl ammonium chloride, dibutyl diicosyldecyl ammonium chloride, or combinations thereof. An embodiment of the invention is one, any or all of prior embodiments in this paragraph up through the first embodiment in this paragraph further comprising separating the alkylation product from the reaction mixture. An embodiment of the invention is one, any or all of prior embodiments in this paragraph up through the first embodiment in this paragraph wherein the alkylation reaction conditions include at least one of a temperature of from −10° to 50° C., a pressure of from 100 kPa to 2100 kPa, or a liquid hourly space velocity of from 0.1 to 60.0 hr$^{-1}$. An embodiment of the invention is one, any or all of prior embodiments in this paragraph up through the first embodiment in this paragraph further comprising increasing a concentration of the sulfuric acid catalyst from a first concentration to a second concentration, and wherein a calculated RON of the alkylation product at the second concentration of the sulfuric acid catalyst is greater than a calculated RON of the alkylation product at the first concentration of the sulfuric acid catalyst. An embodiment of the invention is one, any or all of prior embodiments in this paragraph up through the first embodiment in this paragraph wherein the calculated RON of the alkylation product is at least 2 calculated RON greater than the calculated RON of the alkylation product in the absence of the surfactant. An embodiment of the invention is one, any or all of prior embodiments in this paragraph up through the first embodiment in this paragraph further comprising increasing a concentration of the sulfuric acid catalyst from a first concentration to a second concentration, and wherein a calculated RON of the alkylation product at the second concentration of the sulfuric acid catalyst is greater than a calculated RON of the alkylation product at the first concentration of the sulfuric acid catalyst.

A second embodiment of the invention is a process for sulfuric acid catalyzed alkylation comprising selecting a $C_3$-$C_5$ olefin composition; selecting a concentration of sulfuric acid in an alkylation reaction zone; selecting a concentration of a surfactant based on the $C_3$-$C_5$ olefin composition selected and the sulfuric acid concentration selected; reacting the $C_3$-$C_5$ olefin composition and an isoparaffin in the presence of a sulfuric acid catalyst and the surfactant in the alkylation reaction zone operating at alkylation reaction conditions to form a reaction mixture comprising an alkylation product, the reaction mixture comprising a Winsor Type III phase system, wherein the surfactant has a solubility at 25° C. of 0.5% or less in the $C_3$-$C_5$ olefin composition, the isoparaffin, the sulfuric acid catalyst, and the alkylation product, and wherein a calculated RON of the alkylation product is greater than a calculated RON of an alkylation product reacted in the absence of the surfactant; and separating the alkylation product from the reaction mixture.

A third embodiment of the invention is a process for sulfuric acid catalyzed alkylation comprising selecting a $C_3$-$C_5$ olefin composition; selecting a concentration of a surfactant based on the $C_3$-$C_5$ olefin composition selected, wherein the surfactant comprises a dioctadecyl-dimethyl-ammonium halide; reacting the $C_3$-$C_5$ olefin composition and an isoparaffin in the presence of a sulfuric acid catalyst and the surfactant in the alkylation reaction zone operating at alkylation reaction conditions to form a reaction mixture comprising an alkylation product, the reaction mixture comprising a Winsor Type III phase system, wherein the surfactant has a solubility at 25° C. of 0.5% or less in the $C_3$-$C_5$ olefin composition, the isoparaffin, the sulfuric acid catalyst, and the alkylation product, and wherein a RON of the alkylation product is greater than a RON of an alkylation product reacted in the absence of the surfactant; separating the reaction mixture into a hydrocarbon stream comprising the alkylation product and a bottom stream comprising an emulsion comprising sulfuric acid and the surfactant; separating the hydrocarbon stream into an alkylation product stream and a recycle stream comprising at least one of unreacted isoparaffin and unreacted olefin; recovering the alkylation product stream; and optionally recycling the recycle stream to the alkylation reaction zone; wherein when the $C_3$-$C_5$ olefin composition comprises a linear $C_4$-$C_5$ olefin, the concentration of the surfactant is less than 100 ppmw of the reaction mixture; and when the $C_3$-$C_5$ olefin composition comprises a branched olefin or a mixture of linear and branched olefins, the concentration of the surfactant is greater than or equal to 100 ppmw of the reaction mixture. An embodiment of the invention is one, any or all of prior embodiments in this paragraph up through the third embodiment in this paragraph further comprising increasing a concentration of the sulfuric acid catalyst from a first concentration to a second concentration, and wherein a calculated RON of the alkylation product at the second concentration of the sulfuric acid catalyst is greater than a calculated RON of the alkylation product at the first concentration of the sulfuric acid catalyst.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. A process for sulfuric acid catalyzed alkylation comprising:
   selecting a $C_3$-$C_5$ olefin composition;
   selecting a concentration of a surfactant based on the $C_3$-$C_5$ olefin composition selected; and
   reacting the $C_3$-$C_5$ olefin composition and an isoparaffin in the presence of a sulfuric acid catalyst and the surfactant in the alkylation reaction zone operating at alkylation reaction conditions to form a reaction mixture comprising an alkylation product, the reaction mixture comprising a Winsor Type III phase system, wherein the surfactant has a solubility at 25° C. of 0.5% or less in the $C_3$-$C_5$ olefin composition, the isoparaffin, the sulfuric acid catalyst, and the alkylation product, and wherein a calculated RON of the alkylation product is greater than a calculated RON of an alkylation product reacted in the absence of the surfactant.

2. The process of claim 1 wherein when the $C_3$-$C_5$ olefin composition comprises a linear $C_4$-$C_5$ olefin, the concentration of the surfactant is less than 100 ppmw of the reaction mixture.

3. The process of claim 2 wherein the linear $C_4$-$C_5$ olefin comprises 1-butene, 2-butene, or combinations thereof.

4. The process of claim 2 wherein the concentration of the surfactant is less than 90 ppmw of the reaction mixture.

5. The process of claim 1 wherein when the $C_3$-$C_5$ olefin composition comprises a branched olefin or a mixture of linear and branched olefins, the concentration of the surfactant is greater than or equal to 100 ppmw of the reaction mixture.

6. The process of claim 5 wherein the branched olefins comprise isobutene, or wherein the mixture of linear and branched olefins comprises a mixture of $C_3$ and $C_4$ olefins.

7. The process of claim 5 wherein the mixture of linear and branched olefins comprises a mixture of isobutene, 1-butene, and 2-butene.

8. The process of claim 5 wherein the concentration of the surfactant is greater than or equal to 120 ppmw of the reaction mixture.

9. The process of claim 1 wherein the isoparaffin comprises isobutane, isopentane, or combinations thereof.

10. The process of claim 1 wherein the surfactant comprises a quaternary ammonium cationic salt, or a quaternary phosphonium cationic salt, or combinations thereof.

11. The process of claim 10 wherein the quaternary ammonium cationic salt or a quaternary phosphonium cationic salt comprises a quaternary ammonium halide, a quaternary ammonium sulfate, a quaternary ammonium hydrogen sulfate, a quaternary ammonium nitrate, a quaternary ammonium carbonate, a quaternary ammonium bicarbonate, a quaternary phosphonium halide, a quaternary phosphonium sulfate, a quaternary phosphonium hydrogen sulfate, a quaternary phosphonium nitrate, a quaternary phosphonium carbonate, a quaternary phosphonium bicarbonate, or combinations thereof.

12. The process of claim 1 wherein the surfactant comprises dibutyl dioctyldecyl ammonium chloride, dimethyl dipentadecyl ammonium chloride, diethyl dipentadecyl ammonium chloride, dipropyl dipentadecyl ammonium chloride, dibutyl dipentadecyl ammonium chloride, dimethyl dihexadecyl ammonium chloride, diethyl dihexadecyl ammonium chloride, dipropyl dihexadecyl ammonium chloride, dibutyl dihexadecyl ammonium chloride, dimethyl diheptadecyl ammonium chloride, diethyl diheptadecyl ammonium chloride, dipropyl diheptadecyl ammonium chloride, dibutyl diheptadecyl ammonium chloride, dimethyl dioctadecyl ammonium chloride, diethyl dioctadecyl ammonium chloride, dipropyl dioctadecyl ammonium chloride, dimethyl dinonadecyl ammonium chloride, diethyl dinonadecyl ammonium chloride, dipropyl dinonadecyl ammonium chloride, dibutyl dinonadecyl ammonium chloride, dimethyl diicosylecyl ammonium chloride, diethyl diicosyldecyl ammonium chloride, dipropyl diicosyldecyl ammonium chloride, dibutyl diicosyldecyl ammonium chloride, or combinations thereof.

13. The process of claim 1 further comprising:
separating the alkylation product from the reaction mixture.

14. The process of claim 1 wherein the alkylation reaction conditions include at least one of: a temperature of from −10° to 50° C., a pressure of from 100 kPa to 2100 kPa, or a liquid hourly space velocity of from 0.1 to 60.0 $hr^{-1}$.

15. The process of claim 1 further comprising:
increasing a concentration of the sulfuric acid catalyst from a first concentration to a second concentration, and wherein a calculated RON of the alkylation product at the second concentration of the sulfuric acid catalyst is greater than a calculated RON of the alkylation product at the first concentration of the sulfuric acid catalyst.

16. The process of claim 1 wherein the calculated RON of the alkylation product is at least 2 calculated RON greater than the calculated RON of the alkylation product in the absence of the surfactant.

17. The process of claim 1 further comprising:
increasing a concentration of the sulfuric acid catalyst from a first concentration to a second concentration, and wherein a calculated RON of the alkylation product at the second concentration of the sulfuric acid catalyst is greater than a calculated RON of the alkylation product at the first concentration of the sulfuric acid catalyst.

18. A process for sulfuric acid catalyzed alkylation comprising:
selecting a $C_3$-$C_5$ olefin composition;
selecting a concentration of sulfuric acid in an alkylation reaction zone;
selecting a concentration of a surfactant based on the $C_3$-$C_5$ olefin composition selected and the sulfuric acid concentration selected;
reacting the $C_3$-$C_5$ olefin composition and an isoparaffin in the presence of a sulfuric acid catalyst and the surfactant in the alkylation reaction zone operating at alkylation reaction conditions to form a reaction mixture comprising an alkylation product, the reaction mixture comprising a Winsor Type III phase system, wherein the surfactant has a solubility at 25° C. of 0.5% or less in the $C_3$-$C_5$ olefin composition, the isoparaffin, the sulfuric acid catalyst, and the alkylation product, and wherein a calculated RON of the alkylation product is greater than a calculated RON of an alkylation product reacted in the absence of the surfactant; and
separating the alkylation product from the reaction mixture.

19. A process for sulfuric acid catalyzed alkylation comprising:
selecting a $C_3$-$C_5$ olefin composition;
selecting a concentration of a surfactant based on the $C_3$-$C_5$ olefin composition selected, wherein the surfactant comprises a dioctadecyl-dimethyl-ammonium halide;
reacting the $C_3$-$C_5$ olefin composition and an isoparaffin in the presence of a sulfuric acid catalyst and the surfactant in the alkylation reaction zone operating at alkylation reaction conditions to form a reaction mixture comprising an alkylation product, the reaction mixture comprising a Winsor Type III phase system, wherein the surfactant has a solubility at 25° C. of 0.5% or less in the $C_3$-$C_5$ olefin composition, the isoparaffin, the sulfuric acid catalyst, and the alkylation product, and wherein a RON of the alkylation product is greater than a RON of an alkylation product reacted in the absence of the surfactant;

separating the reaction mixture into a hydrocarbon stream comprising the alkylation product and a bottom stream comprising an emulsion comprising sulfuric acid and the surfactant;

separating the hydrocarbon stream into an alkylation product stream and a recycle stream comprising at least one of unreacted isoparaffin and unreacted olefin;

recovering the alkylation product stream; and optionally recycling the recycle stream to the alkylation reaction zone;

wherein:

when the $C_3$-$C_5$ olefin composition comprises a linear $C_4$-$C_5$ olefin, the concentration of the surfactant is less than 100 ppmw of the reaction mixture; and when the $C_3$-$C_5$ olefin composition comprises a branched olefin or a mixture of linear and branched olefins, the concentration of the surfactant is greater than or equal to 100 ppmw of the reaction mixture.

20. The process of claim 19 further comprising:

increasing a concentration of the sulfuric acid catalyst from a first concentration to a second concentration, and wherein a calculated RON of the alkylation product at the second concentration of the sulfuric acid catalyst is greater than a calculated RON of the alkylation product at the first concentration of the sulfuric acid catalyst.

* * * * *